United States Patent
Frick et al.

(10) Patent No.: US 11,111,204 B2
(45) Date of Patent: Sep. 7, 2021

(54) METHOD FOR PRODUCTION OF METHYL METHACRYLATE BY OXIDATIVE ESTERIFICATION USING A HETEROGENEOUS CATALYST

(71) Applicants: Dow Global Technologies LLC, Midland, MI (US); Rohm and Haas Company, Collegeville, PA (US)

(72) Inventors: Christopher D. Frick, Pottstown, PA (US); Jeffrey A. Herron, Midland, MI (US); Kirk W. Limbach, Dresher, PA (US); Wen Sheng Lee, Midland, MI (US); Victor J. Sussman, Midland, MI (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 0 days.

(21) Appl. No.: 16/959,232

(22) PCT Filed: Dec. 13, 2018

(86) PCT No.: PCT/US2018/065374
§ 371 (c)(1),
(2) Date: Jun. 30, 2020

(87) PCT Pub. No.: WO2019/139720
PCT Pub. Date: Jul. 18, 2019

(65) Prior Publication Data
US 2020/0331840 A1   Oct. 22, 2020

Related U.S. Application Data

(60) Provisional application No. 62/615,504, filed on Jan. 10, 2018.

(51) Int. Cl.
| | | |
|---|---|---|
| *C07C 67/39* | (2006.01) | |
| *B01J 21/06* | (2006.01) | |
| *B01J 21/08* | (2006.01) | |
| *B01J 23/44* | (2006.01) | |
| *B01J 23/52* | (2006.01) | |
| *B01J 35/02* | (2006.01) | |
| *B01J 35/00* | (2006.01) | |
| *B01J 19/18* | (2006.01) | |
| *C07C 69/54* | (2006.01) | |

(52) U.S. Cl.
CPC .............. *C07C 67/39* (2013.01); *B01J 21/063* (2013.01); *B01J 21/08* (2013.01); *B01J 23/44* (2013.01); *B01J 23/52* (2013.01); *B01J 35/008* (2013.01); *B01J 35/023* (2013.01); *B01J 19/1812* (2013.01); *C07C 69/54* (2013.01)

(58) Field of Classification Search
CPC ...... C07C 67/39; C07C 69/54; B01J 19/1812; B01J 35/023; B01J 21/063; B01J 21/08; B01J 23/44; B01J 23/52; B01J 35/008
See application file for complete search history.

(56) References Cited

U.S. PATENT DOCUMENTS

| 7,326,806 | B2 | 2/2008 | Hayashi et al. | |
|---|---|---|---|---|
| 8,461,373 | B2 | 6/2013 | Suzuki et al. | |
| 8,461,737 | B2 | 6/2013 | Feng et al. | |
| 10,232,353 | B2 | 3/2019 | Lygin et al. | |
| 2003/0060655 | A1* | 3/2003 | Hayashi | B01J 35/002 560/238 |
| 2016/0068464 | A1 | 3/2016 | Krill et al. | |

FOREIGN PATENT DOCUMENTS

| JP | 2002361086 | | 12/2002 | |
|---|---|---|---|---|
| JP | 2004 181357 | A * | 7/2004 | ............ B01J 23/52 |
| JP | 2004 181359 | * | 7/2004 | ............ B01J 23/52 |
| JP | 2004181357 | | 7/2004 | |
| WO | 2009022544 | | 2/2009 | |
| WO | 2016113106 | | 7/2016 | |

OTHER PUBLICATIONS

JP 2004181357, Hayshi, T, et al., Method for suppressing S Tripping of gold fine particle, English translation, 18 pages (Year: 2004).*
Otterstatter, R., et al., Three-phase heterogeneously catalyzed oxidative esterification—relevance of oxygen mass transport, Chem. Eng. Technol. vol. 39, No. 11, pp. 2029-2034 (Year: 2016).*
JP 2004181, Hayashi, T., et al., Catalyst for producing carboxylic acid ester and method for producing carboxylic acid ester, English translation, 32 pages (Year: 2004).*

* cited by examiner

*Primary Examiner* — Yate' K Cutliff
(74) *Attorney, Agent, or Firm* — Brian L. Mutschler

(57) ABSTRACT

A method for preparing methyl methacrylate from methacrolein and methanol; said method comprising contacting a mixture comprising methacrolein, methanol and oxygen with a heterogeneous catalyst comprising a support and a noble metal, wherein said support comprises silicon, and wherein said catalyst comprises from 0.1 to 40 mol % titanium and from 0.1 to 10 mol % of at least one noble metal.

9 Claims, No Drawings

METHOD FOR PRODUCTION OF METHYL METHACRYLATE BY OXIDATIVE ESTERIFICATION USING A HETEROGENEOUS CATALYST

BACKGROUND OF THE INVENTION

The invention relates to a method for preparing methyl methacrylate from methacrolein and methanol using a heterogeneous catalyst.

Heterogeneous catalysts having noble metals supported on silica in combination with alumina and other elements are known, see e.g. U.S. Pat. No. 8,461,737B2. However, there is a need for additional catalyst particles with improved properties.

SUMMARY OF THE INVENTION

The present invention is directed to a method for preparing methyl methacrylate from methacrolein and methanol; said method comprising contacting a mixture comprising methacrolein, methanol and oxygen with a heterogeneous catalyst comprising a support and a noble metal, wherein said support comprises silicon, and wherein said catalyst comprises from 0.1 to 40 mol % titanium and from 0.1 to 10 mol % of at least one noble metal, wherein mole percentages are based on total moles of silicon atoms and metal atoms.

DETAILED DESCRIPTION OF THE INVENTION

All percentage compositions are weight percentages (wt %), and all temperatures are in ° C., unless otherwise indicated. A "noble metal" is any of gold, platinum, iridium, osmium, silver, palladium, rhodium and ruthenium. More than one noble metal may be present in the catalyst, in which case the limits apply to the total of all noble metals. A "metal" is an element in groups 1 through 12 of the periodic table, excluding hydrogen, plus aluminum, gallium, indium, thallium, tin, lead and bismuth. The "catalyst center" is the centroid of the catalyst particle, i.e., the mean position of all points in all coordinate directions. A diameter is any linear dimension passing through the catalyst center and the average diameter is the arithmetic mean of all possible diameters. The aspect ratio is the ratio of the longest to the shortest diameters.

Preferably, the support is a particle comprising a refractory oxide; preferably silica, titania, magnesia, or a combination thereof; preferably the support is silica or silica modified with other refractory oxides. Preferably the support has a surface area greater than 10 m$^2$/g, preferably greater than 30 m$^2$/g, preferably greater than 50 m$^2$/g, preferably greater than 100 m$^2$/g, preferably greater than 120 m$^2$/g. Preferably, the support comprises a silica particle comprising from 0.1 to 40 mol % titanium, based on total moles of silicon atoms and metal atoms (i.e., excluding oxygen and other non-metallic elements other than silicon), preferably at least 0.1 mol %, preferably at least 1 mol %; preferably no more than 40 mol %, preferably no more than 30 mol %. Preferably, the support comprises no more than 10 mol % aluminum, based on total moles of silicon atoms and metal atoms, preferably no more than 5 mol %, preferably no more than 2 mol %, preferably no more than 1 mol %, preferably no more than 0.5 mol %.

Preferably, the aspect ratio of the catalyst particle is no more than 10:1, preferably no more than 5:1, preferably no more than 3:1, preferably no more than 2:1, preferably no more than 1.5:1, preferably no more than 1.1:1. Preferred shapes for the particle include spheres, cylinders, rectangular solids, rings, multi-lobed shapes (e.g., cloverleaf cross section), shapes having multiple holes and "wagon wheels," preferably spheres. Irregular shapes may also be used.

Preferably, the catalyst comprises 0.1 to 10 mol % of at least one noble metal, 50 to 95 mol % Si, 0.1 to 40 mol % Ti and 0.1 to 40 mol % alkali metal or alkaline earth metal or a combination thereof, based on total moles of silicon atoms and metal atoms. Preferably, the catalyst comprises at least 55 mol % Si, preferably at least 60 mol %, preferably at least 65 mol %, preferably at least 70 mol %; preferably no more than 97 mol %. Preferably, the catalyst comprises at least 0.1 mol % Ti, preferably at least 1 mol %, preferably at least 5 mol %; preferably no more than 30 mol %, preferably no more than 20 mol %, preferably no more than 15 mol %. Preferably, the catalyst comprises at least 0.1 mol % noble metal(s), preferably at least 0.2 mol %, preferably at least 0.3 mol %; preferably no more than 7 mol %, preferably no more than 5 mol %, preferably no more than 3 mol %. Preferably, the catalyst comprises at least 0.1 mol % alkali or alkaline earth metal(s), preferably at least 1 mol %, preferably at least 2 mol %; preferably no more than 30 mol %, preferably no more than 20 mol %, preferably no more than 15 mol %. In one preferred embodiment of the invention, the catalyst comprises no more than 20 mol % magnesium, based on total moles of silicon atoms and metal atoms, preferably no more than 10 mol %, preferably no more than 5 mol %, preferably no more than 2 mol %, preferably no more than 1 mol %. In one preferred embodiment of the invention, the catalyst comprises no more than 20 mol % alkaline earth metals, based on total moles of silicon atoms and metal atoms, preferably no more than 10 mol %, preferably no more than 5 mol %, preferably no more than 2 mol %, preferably no more than 1 mol %.

Preferably, at least 90 wt % of the noble metal(s) is in the outer 80% of catalyst volume (i.e., the volume of an average catalyst particle), preferably the outer 60%, preferably in the outer 50%, preferably in the outer 40%, preferably the outer 30%, preferably the outer 25%. Preferably, the outer volume of any particle shape is calculated for a volume having a constant distance from its inner surface to its outer surface (the surface of the particle), measured along a line perpendicular to the outer surface. For example, for a spherical particle the outer x % of volume is a spherical shell whose outer surface is the surface of the particle and whose volume is x % of the volume of the entire sphere. Preferably, at least 95 wt % of the noble metal is in the outer volume of the catalyst, preferably at least 97 wt %, preferably at least 99 wt %. Preferably, at least 90 wt % (preferably at least 95 wt %, preferably at least 97 wt %, preferably at least 99 wt %) of the noble metal(s) is within a distance from the surface that is no more than 15% of the catalyst diameter, preferably no more than 10%, preferably no more than 8%, preferably no more than 6%. Distance from the surface is measured along a line which is perpendicular to the surface.

Preferably, the noble metal is gold or palladium, preferably gold.

Preferably, the average diameter of the catalyst particle is at least 60 microns, preferably at least 100 microns, preferably at least 200 microns, preferably at least 300 microns, preferably at least 400 microns, preferably at least 500 microns, preferably at least 600 microns, preferably at least 700 microns, preferably at least 800 microns; preferably no more than 30 mm, preferably no more than 20 mm, preferably no more than 10 mm, preferably no more than 5 mm, preferably no more than 3 mm. The average diameter of the support and the average diameter of the final catalyst particle are not significantly different.

Preferably, the amount of noble metal as a percentage of the noble metal and the support is from 0.2 to 5 wt %, preferably at least 0.5 wt %, preferably at least 0.8 wt %, preferably at least 1 wt %, preferably at least 1.2 wt %; preferably no more than 4 wt %, preferably no more than 3 wt %, preferably no more than 2.5 wt %.

The catalyst of this invention is useful in a process for producing methyl methacrylate (MMA) which comprises treating methacrolein with methanol in an oxidative esterification reactor (OER) containing a catalyst bed. The catalyst bed comprises the catalyst particles and is situated within the OER that fluid flow may occur through the catalyst bed. The catalyst particles in the catalyst bed typically are held in place by solid walls and by screens. In some configurations, the screens are on opposite ends of the catalyst bed and the solid walls are on the side(s), although in some configurations the catalyst bed may be enclosed entirely by screens. Preferred shapes for the catalyst bed include a cylinder, a rectangular solid and a cylindrical shell; preferably a cylinder. The OER further comprises a liquid phase comprising methacrolein, methanol and MMA and a gaseous phase comprising oxygen. The liquid phase may further comprise byproducts, e.g., methacrolein dimethyl acetal (MDA) and methyl isobutyrate (MIB). Preferably, the liquid phase is at a temperature from 40 to 120° C.; preferably at least 50° C., preferably at least 60° C.; preferably no more than 110° C., preferably no more than 100° C. Preferably, the catalyst bed is at a pressure from 0 to 2000 psig (101.3 to 13890.8 kPa); preferably no more than 2000 kPa, preferably no more than 1500 kPa. Preferably, pH in the catalyst bed is from 4 to 10; preferably at least 4.5, preferably at least 5; preferably no greater than 9, preferably no greater than 8, preferably no greater than 7.5, preferably no greater than 7, preferably no greater than 6.5. Preferably, the catalyst bed is in a tubular continuous reactor.

The OER typically produces MMA, along with methacrylic acid and unreacted methanol. Preferably, methanol and methacrolein are fed to the reactor containing the fixed bed in a methanol:methacrolein molar ratio from 1:10 to 100:1, preferably from 1:2 to 20:1, preferably from 1:1 to 10:1. Preferably, the fixed bed further comprises inert materials. Preferred inert materials include, e.g., alumina, clay, glass, silica carbide and quartz. Preferably the inert materials are in the size range for the catalyst or smaller. Preferably, the reaction products are fed to a methanol recovery distillation column which provides an overhead stream rich in methanol and methacrolein; preferably this stream is recycled back to the OER. The bottoms stream from the methanol recovery distillation column comprises MMA, MDA, methacrylic acid, salts and water. In one embodiment of the invention, MDA is hydrolyzed in a medium comprising MMA, MDA, methacrylic acid, salts and water. MDA may be hydrolyzed in the bottoms stream from a methanol recovery distillation column; said stream comprising MMA, MDA, methacrylic acid, salts and water. In another embodiment, MDA is hydrolyzed in an organic phase separated from the methanol recovery bottoms stream. It may be necessary to add water to the organic phase to ensure that there is sufficient water for the MDA hydrolysis; these amounts may be determined easily from the composition of the organic phase. The product of the MDA hydrolysis reactor is phase separated and the organic phase passes through one or more distillation columns to produce MMA product and light and/or heavy byproducts.

Preferably, the catalyst is produced by precipitating on a support particle (preferably silica) titanium from a titanium salt and then the noble metal from an aqueous solution of metal salts in the presence of the support. Preferred titanium salts include titanium acetate, titanium sulfate, titanium(IV) oxysulfate, titanium chloride, titanium oxychloride, titanium (IV) bis(ammonium lactato)dihydroxide solution, titanium (IV) 2-ethylhexyloxide, titanium(IV) butoxide, titanium (IV) isopropoxide and titanium(IV) oxyacetylacetonate. Preferred noble metal salts include tetrachloroauric acid, sodium aurothiosulfate, sodium aurothiomalate, gold hydroxide, palladium nitrate, palladium chloride and palladium acetate. In one preferred embodiment, a titanium-modified support is produced by an incipient wetness technique in which an aqueous solution of a titanium precursor salt is added to a porous inorganic oxide such that the pores are filled with the solution and the water is then removed by drying. Preferably, the resulting material is then treated by calcination, reduction, or other treatments known to those skilled in the art to decompose the titanium salts into metals or metal oxides. Preferably, noble metal(s) is added to the calcined titanium-modified support by incipient wetness, followed by drying, and preferably by calcination.

Calcinations preferably are carried out at a temperature from 250° C. to 600° C.; preferably at least 300° C., preferably no more than 550° C. Preferably, the temperature is increased in a stepwise or continuous fashion to the ultimate calcination temperature.

In another preferred embodiment, the catalyst is produced by deposition precipitation in which a porous inorganic oxide is immersed in an aqueous solution containing a suitable noble metal precursor salt and that salt is then made to interact with the surface of the inorganic oxide by adjusting the pH of the solution. The resulting treated solid is then recovered (e.g. by filtration) and then converted into a finished catalyst by calcination, reduction, or other treatments known to those skilled in the art to decompose the noble metal salts into metals or metal oxides.

EXAMPLES

Example #1

Single Pass Fixed Bed Bubble Column Reactor Operation:

A feed consisting of 20 wt % methacrolein, 200 ppm inhibitor, and a balance of methanol was fed at a rate of 40 g/hr to a ⅜" (9.5 mm) stainless steel tubular reactor containing a short front section of borosilicate glass beads followed by 5 g of catalyst. Catalyst #1 was utilized. A gas containing 8% oxygen in nitrogen was also feed to the reactor at a rate sufficient to obtain 4.5% $O_2$ in the vent. The reactor was operated at 60° C. and 160 psig (1200 kPa). The product of the reactor was sent to a liquid-vapor separator and the vapor was sent to a condenser with liquid return and non-condensable gases going to the vent. Results are described in the below table.

Catalyst #1 Preparation:

Catalyst #1 was prepared by the incipient wetness technique using 20 g of Fuji Silysia Chemical, Ltd. CARiACT Q-10 support as the starting material and adding titanium to the support material. Specifically 10.5 g of titanium isopropoxide along with 3 g of glacial acetic acid were added to the catalyst in rotating equipment to ensure even distribution of the solution to the support material. The solution was at 40° C. when added. The modified support material was then dried under slight vacuum at 60° C. for 4 hrs and then calcined in air at ambient pressure by ramping the temperature at 5° C. per minute from ambient to 125° C., held for 1 hr and then ramped at 5° C. per minute up to 250° C. and held for 1 hr, then ramped at 5° C. per minute to 350° C. and held for 1 hr and finally ramped at 5° C. per minute to 450° C. and held for 4 hrs. Gold was then added to the support by incipient wetness technique utilizing 0.83 g of sodium aurothiosulfate in 10 g of deionized water at 40° C. The resulting catalyst was dried and calcined in air using the same heating profile as above. Analysis with a scanning electron microscope (SEM) equipped with energy-dispersive spectroscopy (EDS) of the catalyst clearly indicates that an eggshell deposition of both Ti and Au exists with the Au preferentially located only where Ti was deposited. The Ti and Au eggshell thickness was found to be approximately 50 microns or less. With an estimated loading of 10 mol % in the outer 50 microns of the 1 mm diameter catalyst, the local loading of titanium is estimated as up to 40 mol % as Ti/(Ti+Si).

Example #2 Comparative

Batch Recycle Fixed Bed Bubble Column Reactor Operation:

A feed solution of 150 g was prepared comprising 10 wt % methacrolein, 200 ppm inhibitor and a balance of methanol, and placed in a 300 ml PARR® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" (6.4 mm) stainless steel tube maintained at 60° C. using an external heater. The reactor itself was packed with 2 mm glass beads to fill approximately 18 inches (46 cm) of the tube, then catalyst. The remaining void at the top of the reactor was filled with 3 mm glass beads. Liquid and gas exiting the top of the reactor were sent to a condenser and non-condensable gases were vented, while the liquid was recycled back into the gas-disengagement vessel. Catalyst #2, as well as the catalysts from examples #3, #4, and #5 below were run in this manner Catalyst #2 Preparation:

Catalyst #2 was prepared by incipient wetness of 4.1 g sodium gold thiosulfate dissolved in 100 g of water to make an aqueous solution and then placed on 100 g of Fuji Silysia Chemical, Ltd. CARiACT Q-20 silica support material. The sample was dried at 120° C. for 1 hr followed by calcination at 400° C. for 4 hr.

Example #3

Catalyst #3 Preparation:

Catalyst #3 was prepared by the following steps. First, a titanium precursor stock solution consisting of 51.7 g of titanium isopropoxide and 28.5 g glacial acetic acid was mixed and stirred at ambient temperature. A support material was then prepared by impregnating 27.9 g of the above mentioned titanium stock solution to the incipient wetness point of 20 g of Fuji Silysia Chemical, Ltd. CARiACT Q-10 silica support material. The sample was then dried at 125° C. for 1 hr, followed by calcination at 250° C. for 1 hr, 350° C. for 1 hr, and 450° C. for overnight with a ramping rate of 5° C. per minute between different temperature settings. Gold deposition was achieved by impregnating a solution containing 0.4 g of sodium gold thiosulfate and 16 g of deionized water to 10 g of the above described support material to its incipient wetness point. The sample was then dried at 120° C. for 1 hr followed by calcination at 400° C. for 4 hr. Analysis with a scanning electron microscope (SEM) equipped with energy-dispersive spectroscopy (EDS) of the catalyst clearly indicates that an eggshell deposition of both Ti and Au exists with the Au preferentially located only where Ti was deposited. The Ti and Au eggshell thickness was found to be approximately 300 microns or less.

Example #4

Catalyst #4 Preparation:

Catalyst #4 was prepared by the following steps. First, a support material was prepared by impregnating titanium isopropoxide to the incipient wetness point of 10 g of Fuji Silysia Chemical, Ltd. CARiACT Q-10 silica support material. The sample was then dried at 125° C. for 1 hr, followed by calcination at 250° C. for 1 hr, 350° C. for 1 hr, 450° C. for 1 hr and 550° C. for 12 hrs with a ramping rate of 5° C. per minute between different temperature settings. Gold deposition was achieved by impregnating a solution containing 0.25 g of sodium gold thiosulfate and 9 g of deionized water to the incipient wetness point of 6 g of the above described support material. The sample was then dried at 120° C. for 1 hr followed by calcination at 400° C. for 4 hrs.

Example #5

Catalyst #5 Preparation:

Catalyst #5 was prepared by the following steps. First, a support material was prepared by impregnating magnesium nitrate hexahydrate to the incipient wetness point of 10 g of Fuji Silysia Chemical, Ltd. CARiACT Q-10 silica support material. The sample was then dried at 120° C. for 1 hr, followed by calcination at 450° C. for 4 hrs with a ramping rate of 5° C. per minute between different temperature settings. A quantity of 8.5 g of titanium isopropoxide and 1.5 g of acetic acid were mixed to provide a titanium precursor solution and 3.1 g of the titanium precursor solution was then impregnated to the above mentioned calcined Mg—SiO$_2$. The sample was then dried at 120° C. for 1 hr, followed by calcination at 550° C. for 6 hrs with a ramping rate of 5° C. per minute between different temperature settings. Gold deposition was achieved by impregnating a solution containing 0.3 g of sodium gold thiosulfate and 8 g of deionized water to the incipient wetness point of 8 g of the above described support material. The sample was then dried at 120° C. for 1 hr followed by calcination at 400° C. for 4 hrs. The resulting sample contained a total of 4.7 wt % Mg and 4 wt % Ti on Si with 1.5 wt % Au loaded on that material. The sample was not assessed to determine if eggshell deposition existed.

| Catalyst # | Catalyst Description | Catalyst Load (g) | Reactor Type | STY (mol/kg-hr) | MIB (ppm) | Normalized MMA Selectivity (%) |
|---|---|---|---|---|---|---|
| 1 | Au/Ti-SiO$_2$ | 5 | Single Pass | 4.9 | 225 | 98.4 |
| 1 | Au/Ti-SiO$_2$ | 1 | Batch | 4.6 | 130 | 98.4 |
| 2 (comp.) | Au/SiO$_2$ | 2 | Batch | 1.75 | 400 | 99.1 |

-continued

| Catalyst # | Catalyst Description | Catalyst Load (g) | Reactor Type | STY (mol/kg-hr) | MIB (ppm) | Normalized MMA Selectivity (%) |
|---|---|---|---|---|---|---|
| 3 | Au/Ti-SiO$_2$ | 1 | Batch | 3.3 | 160 | 94.8 |
| 4 | Au/Ti-SiO$_2$ | 1 | Batch | 3.4 | 140 | 98.9 |
| 5 | Au/Ti-Mg-SiO$_2$ | 1 | Batch | 5.5 | 675 | 98.9 |

* The normalized MMA selectivity is the percent MMA among products originating as methacrolein reactant. MIB is reported in ppm by weight on a 100% MMA product basis.

Crush Strength:

The mechanical strength of catalyst or catalyst support particles was directly measured by crushing the particles to the point of mechanical failure. Crush strength testing was carried out using a Mecmesin M100EC. A single particle was placed on the platform and the top plunger was allowed to press on the particle until the load reached a peak value and the material failed. The peak load was recorded using a Shimpo FGE-100× gauge. The test was repeated on 25 individual particles to obtain a statistical average of the crush strength for any given material. Results are tabulated below.

| Catalyst # | Material Description | Diameter (mm) | Crush force (Newton) | Crush Strength (N/mm) |
|---|---|---|---|---|
| na | Q-10 | 2.6 | 51 | 20 |
| 2 (comp.) | Au/SiO$_2$ | 3.3 | 40 | 12 |
| 3 | Au/Ti—SiO$_2$ | 3.2 | 60 | 19 |
| 5 | Au/Ti—Mg—SiO$_2$ | 3.2 | 24 | 8 |

The invention claimed is:

1. A method for preparing methyl methacrylate from methacrolein and methanol; said method comprising contacting a mixture comprising methacrolein, methanol and oxygen with a heterogeneous catalyst comprising a support and a noble metal, wherein said support comprises silicon, and wherein said catalyst comprises from 0.1 to 40 mol % titanium and from 0.1 to 10 mol % of at least one noble metal selected from the group consisting of gold, platinum, iridium, osmium, silver, palladium, rhodium, and ruthenium, wherein mole percentages are based on total moles of silicon atoms and metal atoms, wherein at least 90 wt % of the noble metal is in the outer 60% of catalyst volume.

2. The method of claim 1 in which the noble metal is selected from the group consisting of gold, palladium and combinations thereof.

3. The method of claim 1 in which the catalyst has an average diameter from 60 microns to 10 mm.

4. The method of claim 1 in which the catalyst comprises 0.1 to 8 mol % of at least one noble metal, 60 to 95 mol % silicon, 0.1 to 20 mol % titanium and 0.1 to 20 mol % alkali metal or alkaline earth metal.

5. The method of claim 1 in which the support is silica.

6. The method of claim 1 in which the noble metal is gold.

7. The method of claim 1 in which the catalyst is contained in a catalyst bed.

8. The method of claim 7 in which methanol and methacrolein are fed to a reactor containing the catalyst bed in a molar ratio from 1:1 to 10:1, respectively.

9. The method of claim 8 in which the reactor is a tubular continuous reactor.

* * * * *